United States Patent
Son

(10) Patent No.: US 9,275,298 B2
(45) Date of Patent: Mar. 1, 2016

(54) MATERIAL CLASSIFICATION USING SPECULAR GLOSS

(71) Applicant: Canon Kabushiki Kaisha, Tokyo (JP)

(72) Inventor: Hui Seong Son, San Jose, CA (US)

(73) Assignee: CANON KABUSHIKI KAISHA, Tokyo (JP)

(*) Notice: Subject to any disclaimer, the term of this patent is extended or adjusted under 35 U.S.C. 154(b) by 68 days.

(21) Appl. No.: 14/255,747

(22) Filed: Apr. 17, 2014

(65) Prior Publication Data

US 2015/0302269 A1   Oct. 22, 2015

(51) Int. Cl.
*G06K 9/46* (2006.01)
*G01N 21/57* (2006.01)

(52) U.S. Cl.
CPC ............ *G06K 9/4647* (2013.01); *G01N 21/57* (2013.01); *G01N 2201/061* (2013.01); *G01N 2201/12* (2013.01)

(58) Field of Classification Search
None
See application file for complete search history.

(56) References Cited

U.S. PATENT DOCUMENTS

| 3,380,334 | A | 4/1968 | Fischer | |
|---|---|---|---|---|
| 3,747,755 | A | 7/1973 | Senturia et al. | |
| 3,829,218 | A * | 8/1974 | Alyanak | G01J 3/2823 356/300 |
| 6,555,822 | B1 | 4/2003 | Zoidis | |
| 7,113,272 | B2 | 9/2006 | Bourely et al. | |
| 7,918,343 | B2 * | 4/2011 | Bohlig | B03B 9/062 209/12.1 |
| 8,421,856 | B2 * | 4/2013 | Sinram | B07C 5/342 348/91 |
| 2004/0008244 | A1 * | 1/2004 | Tsujimoto | G01N 21/57 347/105 |
| 2006/0102528 | A1 * | 5/2006 | Bourely | B07C 5/3416 209/576 |
| 2006/0133650 | A1 * | 6/2006 | Xie | B41J 11/009 382/108 |
| 2007/0076074 | A1 * | 4/2007 | Zhang | B41J 11/009 347/101 |
| 2007/0148047 | A1 * | 6/2007 | Itsuji | G01N 21/35 422/82.11 |
| 2012/0276177 | A1 * | 11/2012 | Hilliard, Jr. | A61K 8/0245 424/401 |
| 2014/0203177 | A1 * | 7/2014 | Kinugawa | G01N 21/3563 250/339.11 |

FOREIGN PATENT DOCUMENTS

| EP | 0 130 715 B1 | 11/1989 |
|---|---|---|
| EP | 0 441 012 A2 | 8/1991 |
| EP | 0 673 289 B1 | 1/1997 |
| WO | 2013/027083 A1 | 2/2013 |
| WO | 2013/086608 A1 | 6/2013 |

OTHER PUBLICATIONS

G. Healey, "Using color for geometry-insensitive segmentation", J. Opt. Soc. Am A., vol. 6, No. 6, pp. 920-937, 1989.
H. Chen, et al., "Polarization Phase-Based Method for Material Classification in Computer Vision", Int. J. of Comp. Vis., vol. 28, No. 1, pp. 73-83, 1998.

* cited by examiner

*Primary Examiner* — Sean Motsinger
(74) *Attorney, Agent, or Firm* — Fitzpatrick, Cella, Harper & Scinto

(57) ABSTRACT

Gloss-based material classification of an object fabricated from an unknown material, particularly where the unknown material is one from a limited set of predetermined materials. The object is illuminated with an area light source such that the object is illuminated from multiple angles. An image of the object is obtained, and specular reflections from the object are measured by analyzing the image. The object material is classified based on a number of high-intensity specular reflections.

19 Claims, 5 Drawing Sheets

MATERIAL CLASSIFICATION USING SPECULAR GLOSS

FIELD

The present disclosure relates to material classification, and in particular relates to classification of an object fabricated from an unknown material.

BACKGROUND

In the field of material classification it is common to use a classification pipeline, in which materials are classified according to color. For example, in a recycling pipeline, spectral colors of different objects can be used to sort the objects for different types of recycling (e.g., paper vs. aluminum).

SUMMARY

One difficulty with the above arrangement is that some objects are difficult to classify using spectral color or other conventional means. In particular, objects composed of different materials that have similar color properties are difficult to distinguish.

The foregoing situation is addressed by classifying an object fabricated from an unknown material based on specular reflections measured when the object is subjected to illumination by an area light source (such as an array of multiple light sources), which illuminates the object from several angles.

Thus, an example embodiment described herein performs material classification of an object fabricated from an unknown material. The object is illuminated with an area light source such as an array of multiple light sources, so that the object is illuminated from multiple angles. A grayscale image of the object is obtained. Specular reflections from the object are measured by analyzing the grayscale image. The object is classified based on the measured intensity of the specular reflections, commonly referred to as glossiness.

By classifying objects based on specular reflections measured when the object is subjected to illumination by an area light source which illuminates the object from several angles, it is ordinarily possible to classify objects composed of different materials that have similar color properties that are difficult to distinguish, and which otherwise might be left unknown. Moreover, by illuminating the object with an area light source, the object is illuminated from multiple different angles such that if the object is glossy and is likely to emit specular reflections, the number and intensity of specular reflections is enhanced.

In one example aspect, the classification is based on whether the number of high intensity specular reflections is large or the number of high intensity specular reflections is small.

In another example aspect, the classifying includes generating a histogram of intensity values of the specular reflections, and differentiating the object from another object by comparing a value of a statistical metric of the object against a value of the statistical metric of another object. In example aspects described herein, the statistical metric is kurtosis, skewness, or an average intensity of a percentage of pixel values of the histogram. In another aspect, the grayscale image is processed to increase contrast prior to generating the histogram.

In still another aspect, the area light source includes an array of multiple light sources.

In yet another aspect, differentiation is performed between objects fabricated from materials which have similar spectral signatures but are formed from different materials. For example, differentiation is performed between similarly-colored objects such as black-colored objects.

In another aspect, an earlier stage of a multi-stage classification process performs material classification based on spectral signatures, and indeterminate objects are delivered for classification according to the embodiment.

In still another aspect, multiple objects are simultaneously classified.

This brief summary has been provided so that the nature of this disclosure may be understood quickly. A more complete understanding can be obtained by reference to the following detailed description and to the attached drawings.

DETAILED DESCRIPTION

Figure 1:
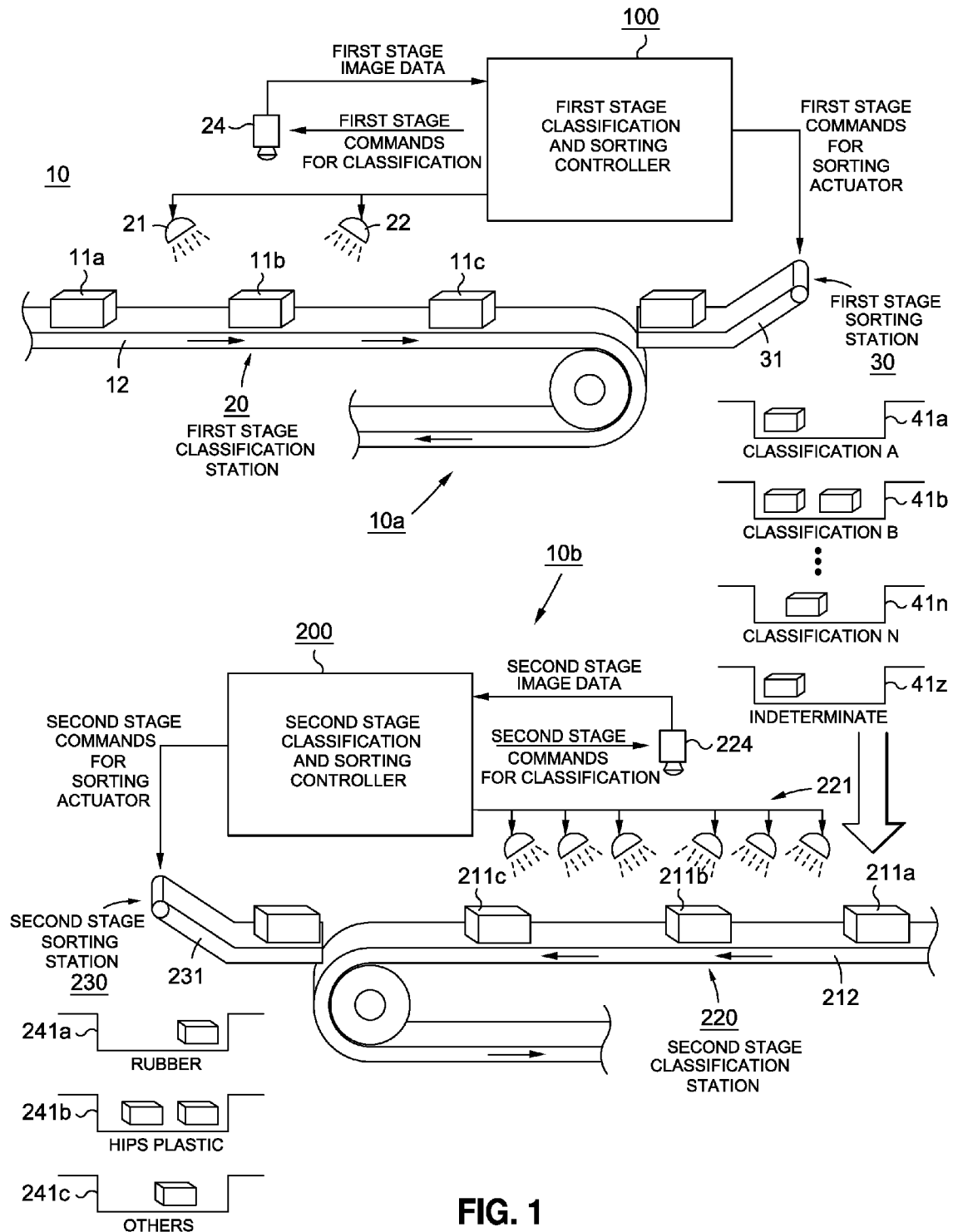
FIG. 1 is an example embodiment of a two-stage classification system according to one description herein, in the form of a recycling system in which objects to be recycled are classified according to the materials from which the objects are fabricated, and the classified objects are sorted for recycling according to their material classification.

FIG. 1 is an example embodiment of a two-stage classification system according to the description herein, in the form of a recycling system 10 in which objects to be recycled are classified according to the materials from which the objects are fabricated, and the classified objects are sorted for recycling according to their material classification. As shown in FIG. 1, recycling system 10 includes a first stage classification system 10a including first stage classification and sorting controller 100, and a second stage classification system 10b including second stage classification and sorting controller 200.

Both of the first and second stage classification systems 10a and 10b operate to perform material classification of an object fabricated from an unknown material. The first stage classification system of this example embodiment performs material classification using spectral reflection characteristics of the object. The objects are sorted based on material classification into multiple different classification categories, such as classification A shown at 41a, classification B shown at 41b, and so on through classification N shown at 41n. Such classifications might, for example, include classification into different metals such as classification into brass, copper and aluminum, and/or might include classification into differently-colored papers and/or differently colored plastics and glass.

At least in part because the first stage classification system 10a performs material classification using spectral reflectance, it may be difficult for the first stage classification system to differentiate between different materials having similar spectral reflectance signatures. As one example, it may be difficult to classify as between different materials that are colored black, due in part because black-colored materials have similar spectral reflectance signatures. Such objects are sorted by the first stage classification system 10a into an indeterminate category at 41z, for further classification by the second stage classification system 10b.

The second stage classification system 10b performs material classification of an object fabricated from an unknown material, in which the objects tend to be similarly-colored or have similar spectral reflectance signatures. Briefly, the objects are subjected to illumination by an area light source such as an array of multiple light sources, and specular reflections from the objects are measured. Material classification is effected based on whether the number of high-intensity specular reflections is large or the number of high-intensity specular reflections is small. In that regard, the number of high-intensity specular reflections gives an indication of glossiness. In one example, histograms may be formed for pixel intensities of captured images, and statistical analysis of the histograms may be used for differentiation between materials. The use of area illumination ensures that glossy objects, which are more likely to form specular reflections than matte objects, are illuminated from a sufficiently large number of angles so as to enhance the occurrence of specular reflections. As such, the second stage classification system 10b is effective at differentiating between different materials having similar spectral reflectance signatures but different glossiness properties, such as black objects fabricated from black rubber on the one hand, and black objects fabricated from HIPS plastic on the other. Such objects may be sorted into bins 241a and 241b as shown in FIG. 1, with other objects being sorted into further bins such as at 241c.

Generally, the first stage classification system 10a may be formed in accordance with the description provided in U.S. application Ser. No. 14/092,492, "Material Classification Using Spectral BRDF Slices", filed Nov. 27, 2013, which is incorporated herein by reference as if set forth in full.

As generally described in the aforementioned application, objects 11a, 11b, etc. are conveyed on a first stage conveyor mechanism 12 to a first stage classification station 20, where the objects are classified according to their material, and thence to a first stage sorting station 30, where the objects are sorted according to their material classification. First stage classification station 20 includes plural light sources 21 and 22, together with a first stage camera 24 for capturing images of objects positioned at first stage classification station 20. The object at the first stage classification station is illuminated individually by each of the plural light sources under control of first stage classification and sorting controller 100, and first stage camera 24 captures one or more images for each individual illumination. Under control of the first stage classification and sorting controller 100, a classification is made for the material from which the object is fabricated.

First stage conveyor mechanism 12 continues to convey the object to first stage sorting station 30, where first stage sorting actuator 31 sorts the objects according to the material classification. Sorting is controlled by first stage classification and sorting controller 100, which commands first stage actuator mechanism 31 to sort the classified objects into multiple receptacles 41a, 41b and 41b and so on through receptacle 41n.

Indeterminate materials that the first stage classification system is unable to differentiate and/or to classify are sorted into bin 41z, and thence delivered to the second stage classification system 10b.

As shown in FIG. 1, in the second stage, objects 211a, 211b and 211c are conveyed on a second stage conveyor mechanism 212 to a second stage classification station 220, where the objects are classified according to their material, and thence to a second stage sorting station 230, where the objects are sorted according to their material classification. Second stage classification station 220 includes an area light source 221 such as multiple light sources arranged in an array, together with a second stage camera 224 for capturing images of objects positioned at second classification station 220. The object at the second stage classification station is illuminated by the area light source 221 under control of second stage classification and sorting controller 200, and the second stage camera 224 captures one or more images of the illuminated object. Under the control of the second stage classification and sorting controller 200, a classification is made of the material from which the object is fabricated.

Second stage conveyor mechanism 212 continues to convey the object to second stage sorting station 230, where second stage sorting actuator 231 sorts the object according to the material classification. Sorting is controlled by second stage classification and sorting controller 200, which commands second stage actuator mechanism 231 to sort the classified objects into multiple receptacles 241a, 241b and 241c.

Thus, as described herein, an earlier stage of a multi-stage classification process performs material classification based on spectral signatures, and indeterminate objects are delivered for classification according to the embodiment. In the second stage, for example, differentiation can be performed between objects fabricated from materials which have similar spectral signatures but are formed from different materials. In one specific example, differentiation is performed between black-colored objects.

Figure 2:
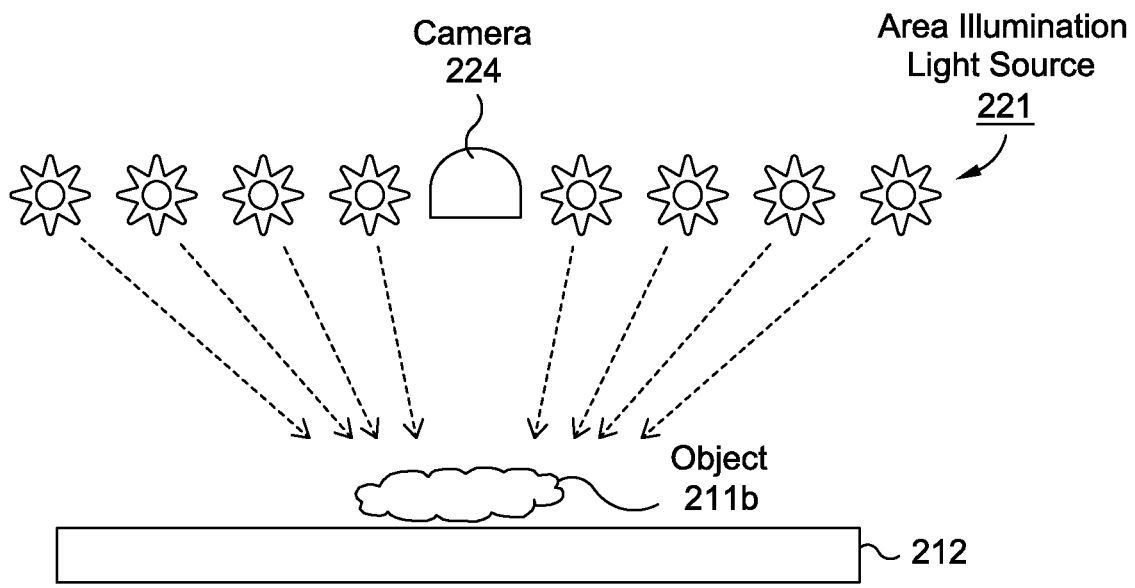
FIG. 2 is a more detailed view of an object being subjected to classification at a second stage classification station of the FIG. 1 view.

FIG. 2 is a more detailed view of an object on conveyor mechanism 212 at second stage classification station 220. In this figure, object 211b is subjected to illumination by area illumination light source 221, which in this embodiment is an array of multiple light sources, and an image of the object is captured by camera 224. In one example, the area illumination is broad-band visible light illumination, and camera 224 is an RGB camera which captures color or grayscale images in the visible light spectrum, with RGB and/or grayscale values for each pixel of the image. Meanwhile, the multiple light sources of the area light source 221 ordinarily ensure that the object is illuminated from a sufficiently large number of angles, so that camera 224 is able to capture sufficient specular reflections to classify the object, even from arbitrarily shaped objects.

In that regard, camera 224 may capture a grayscale image directly, whereas in other examples, camera 224 may convert or transform a color image to a grayscale image. Camera 224 may also transform or convert the RGB image to another color space indicative of intensity, such as Hue-Saturation-Luminance (HSV) or a LAB color space. In addition, camera 224 may capture a color image in order to segment multiple objects being examined simultaneously, and then may convert the segmented images of each object into grayscale images to classify each object, as described below with respect to FIG. 4.

Figure 3:
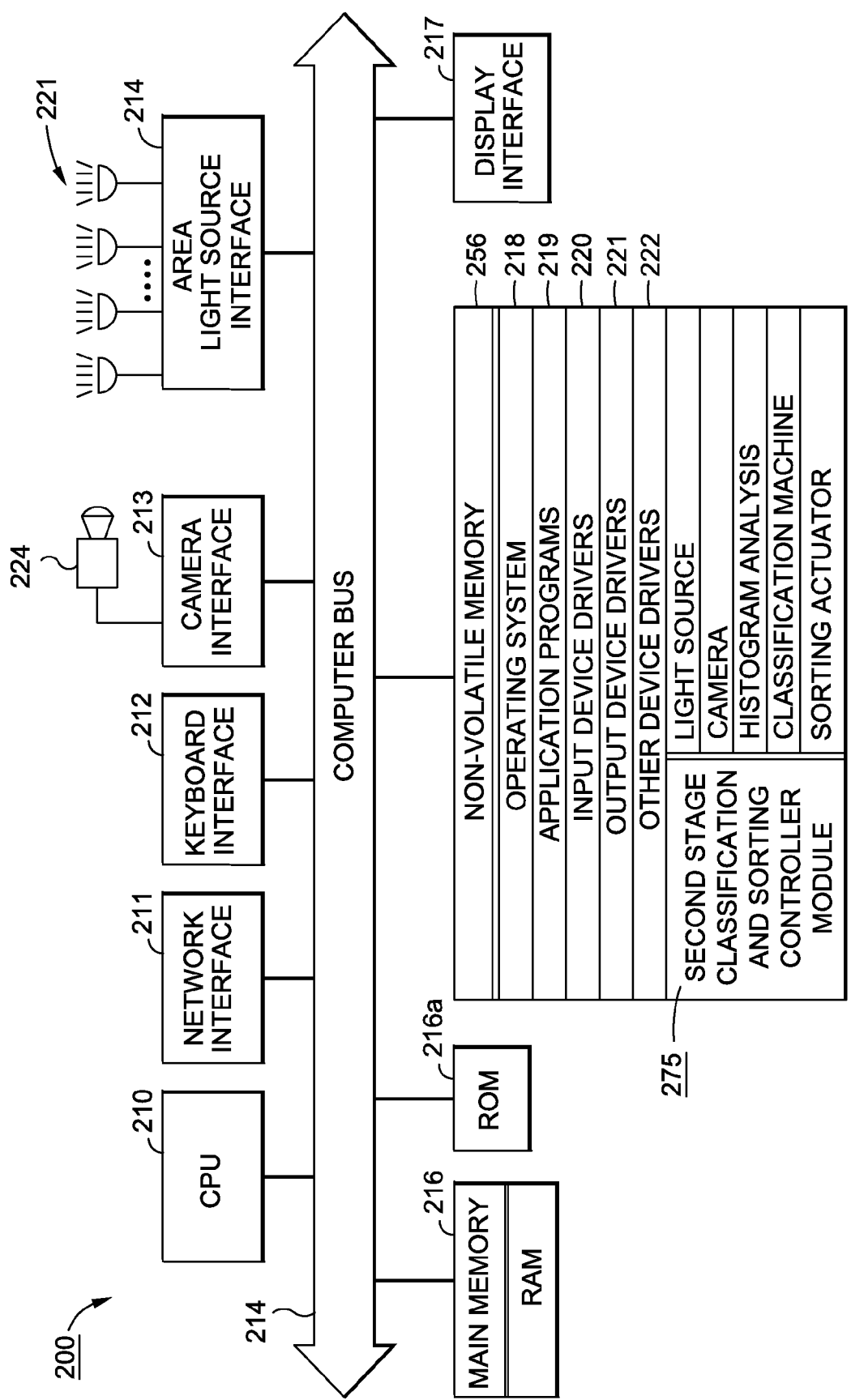
FIG. 3 is a view for explaining the architecture of a second stage classification and sorting controller.

FIG. 3 is a view for explaining the architecture of second-stage classification and sorting controller 200.

As shown in FIG. 3, second stage classification and sorting controller 200 includes central processing unit (CPU) 210 which interfaces with computer bus 214. Also interfacing with computer bus 214 are non-volatile memory 256 (e.g., a hard disk or other nonvolatile, non-transitory storage medium), network interface 211, keyboard interface 212, camera interface 213, random access memory (RAM) 216 for use as a main run-time transient memory, read only memory (ROM) 216a, and display interface 217 for a display screen or other output.

RAM 216 interfaces with computer bus 214 so as to provide information stored in RAM 216 to CPU 210 during execution of the instructions in software programs, such as an operating system, application programs, image processing modules, and device drivers. More specifically, CPU 210 first loads computer-executable process steps from non-volatile memory 256, or another storage device into a region of RAM 216. CPU 210 can then execute the stored process steps from RAM 216 in order to execute the loaded computer-executable process steps. Data also can be stored in RAM 216 so that the data can be accessed by CPU 210 during the execution of the computer-executable software programs, to the extent that such software programs have a need to access and/or modify the data.

As also shown in FIG. 3, non-volatile memory 256 contains computer-executable process steps for operating system 218, and application programs 219, such as programs for monitoring status and for display of status of the second stage. Non-volatile memory 256 also contains computer-executable process steps for device drivers for software interface to devices, such as input device drivers 220, output device drivers 221, and other device drivers 222.

Non-volatile memory 256 also stores a module for second stage classification and sorting controller module 275. The module comprises computer-executable process steps stored on a non-transitory computer readable storage medium such as non-volatile memory 256, wherein the process steps operate to control the area light source 221, camera 224 and sorting actuator 231. According to such control, objects fabricated from an unknown material are subjected to an illumination by area light source 221, and specular reflections from the object are measured using camera 224. Material classification is effected based on whether the number of high-intensity specular reflections is large or the number of high-intensity specular reflections is small. For this purpose and other purposes, a module may be provided for histogram analysis, whereby intensity values of image pixels captured by camera 224 are formed into histograms, and statistical metrics such as kurtosis and skewness are applied against the histogram. For this and other purposes, a classification machine may be trained so as to differentiate between materials based on the captured images, including for example the histograms and the statistical metrics derived from the histograms.

The computer-executable process steps for these modules may be configured as part of operating system 218, as part of an output device driver in output device drivers 221, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

Figure 4:
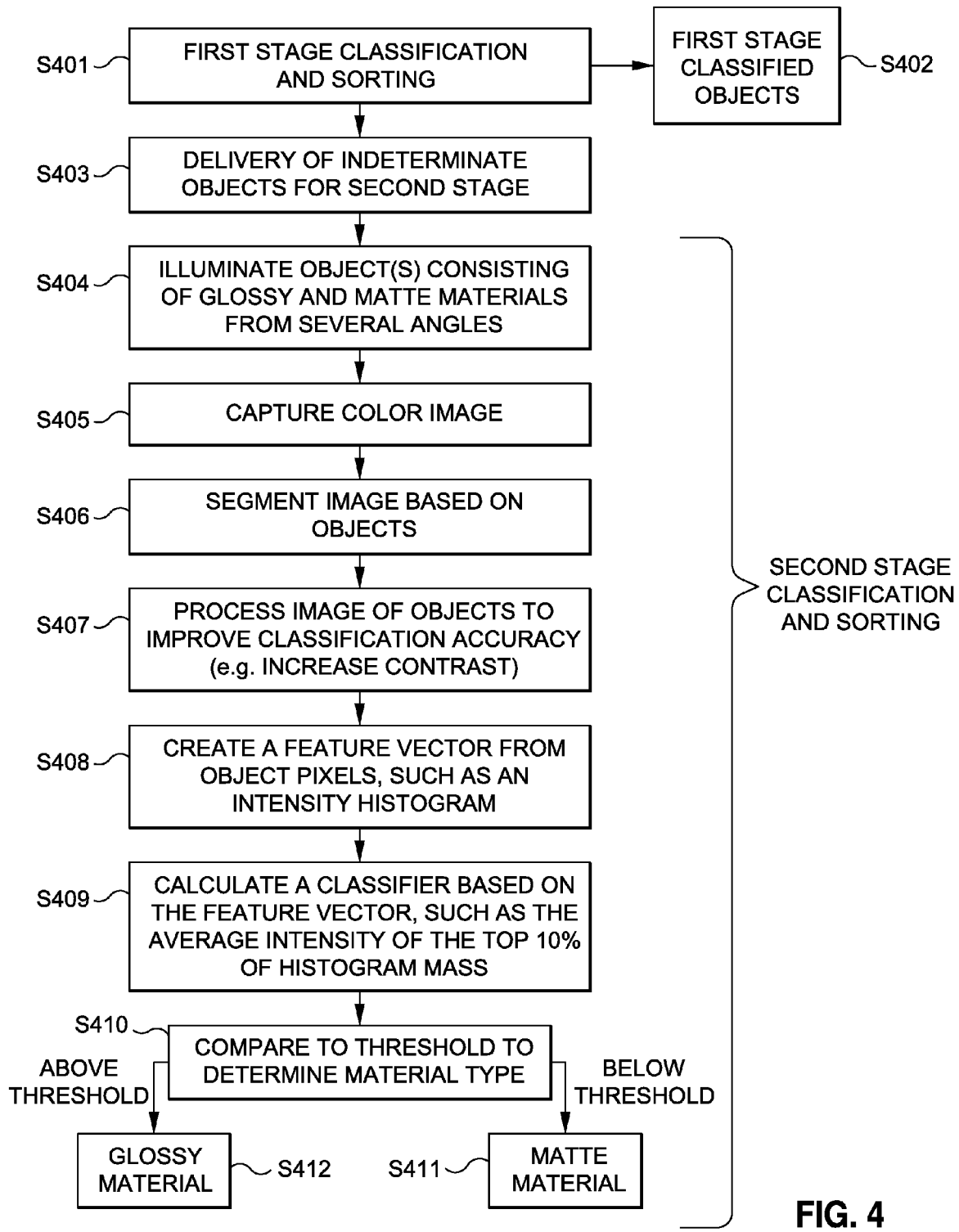
FIG. 4 is a flow diagram illustrating the general flow of processing performed by the second stage classification and sorting controller.

FIG. 4 is a flow diagram illustrating the general flow of processing performed by the second stage classification and sorting controller.

Briefly, in FIG. 4, material classification is performed, of an object fabricated from an unknown material. The object is illuminated with an area light source comprising multiple light sources, and the object is illuminated from multiple angles. A grayscale image of the object is captured. Specular reflections from the object are measured by analyzing the grayscale image. The object is classified based on the measured specular reflections.

In this regard, FIG. 4 describes material classification in the context of classifying several objects in parallel, as described more fully below with respect to FIG. 7. Nevertheless, it should be understood that the material classification described below could also be applied to a situation where objects are classified alone, or where multiple objects are classified one at a time, in series (e.g., by capturing a separate image of each object).

In step S401, first stage classification and sorting is performed, as described above with respect to FIG. 1. In particular, first stage classification and sorting may perform material classification using spectral reflection characteristics of the object, such as spectral signatures.

As a result of step S401, one or more objects may be classified as first stage classified objects in step S402. In particular, some objects can be easily classified by spectral reflection characteristics, and as a result do not require further second stage classification. For example, different metals such as brass, copper and aluminum, differently-colored papers and/or differently colored plastics and glass might be adequately classified from spectral reflection characteristics alone. Nevertheless, other objects, such as black-colored objects, may be difficult or impossible to classify using spectral reflection characteristics, and for these objects, the process proceeds to step S403.

In step S403, indeterminate objects, i.e., those that could not be classified during the first stage, are delivered for the second stage of processing. For example, as discussed above with respect to FIG. 1, objects which have been determined to be indiscriminate might be conveyed by second stage conveyor mechanism 212 to a second stage sorting station 230.

In step S404, the one or more indeterminate objects consisting of, for example, glossy and matte materials such as black rubber and black plastic, are illuminated by multiple light sources from several angles. For example, the object(s) may be illuminated from multiple angles by an area light source including an array of multiple light sources. By virtue of this arrangement, it is ordinarily possible to ensure that the camera (e.g., camera 224) captures several specular reflections from each object, even if the object is arbitrarily shaped.

In that regard, an example of such illumination is illustrated in FIG. 2, described above. In the example shown in FIG. 2, object 211b is subjected to illumination by area illumination light source 221, which in this embodiment is an array of multiple light sources from multiple angles. In one example, the area illumination is broad-band visible light illumination.

In step S405, a color image of the objects is captured by the camera. As described below, classification in the second stage is performed using a grayscale or other intensity image. Nevertheless, in the context of classifying multiple objects at once, a color image can be used to segment the image into images of each object, which are then converted to individual grayscale images.

Thus, in step S406, the image is segmented based on objects. Put another way, the color image is used to segment the image of multiple objects into respective separate images for each object. For example, image processing techniques such as chroma-keying can be used to segment the color image into respective images for each object.

In step S407, each respective image of each object is processed to improve classification accuracy. In particular, a grayscale image of each object may be obtained by converting or transforming the RGB image of each object, although a grayscale image may also be captured directly by, for example, capturing an image in a black-and-white mode. At any rate, each object can be classified at the second stage by using its grayscale image (or another intensity image).

Taking a grayscale image of the object, a reflectively flat material such as black rubber will appear as an evenly black object, whereas a glossy material such as black high impact polystyrene (HIPS) will contain black regions where no specular reflections are captured, mixed with white regions where specular reflections of the light source create intensely illuminated regions.

Figure 5:
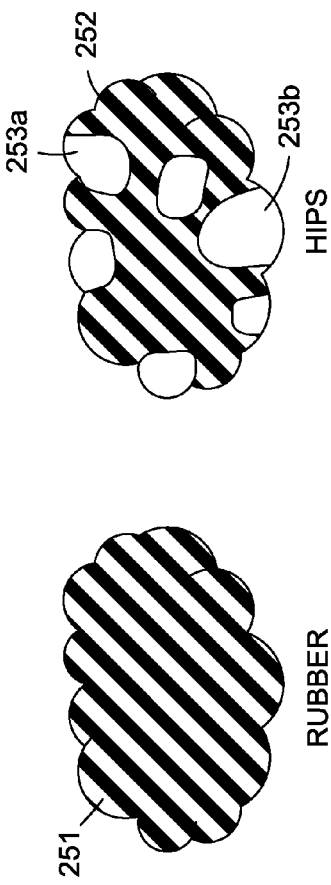
FIG. 5 is a view for explaining differences in specular reflection for objects having similar spectral reflection characteristics, such as differences in specular reflection between an object formed of black rubber and an object formed of black high impact polystyrene (HIPS).

In this regard, FIG. 5 is a view for explaining differences in specular reflection for objects having similar reflection characteristics, such as differences in specular reflection between an object formed of black rubber and an object formed of black high impact polystyrene (HIPS).

As shown in FIG. 5, rubber object 251 appears evenly black in the grayscale image, whereas HIPS object 252 is generally black, but includes white regions such as 253 and 253b where specular reflections of the light source create intensely illuminated regions.

Returning to FIG. 4, in step S407, the raw grayscale images can be processed using techniques such as equalization to, for example, increase contrast for better classification accuracy. Thus, in this example, a grayscale image is processed to increase contrast prior to generating a feature vector such as a histogram.

In step S408, a feature vector, such as an intensity histogram, is created from the object pixels of the grayscale image. An intensity histogram is one helpful way of differentiating lower-intensity specular reflections from higher-intensity specular reflections, thereby to determine the number of high-intensity specular reflections.

Figure 6:
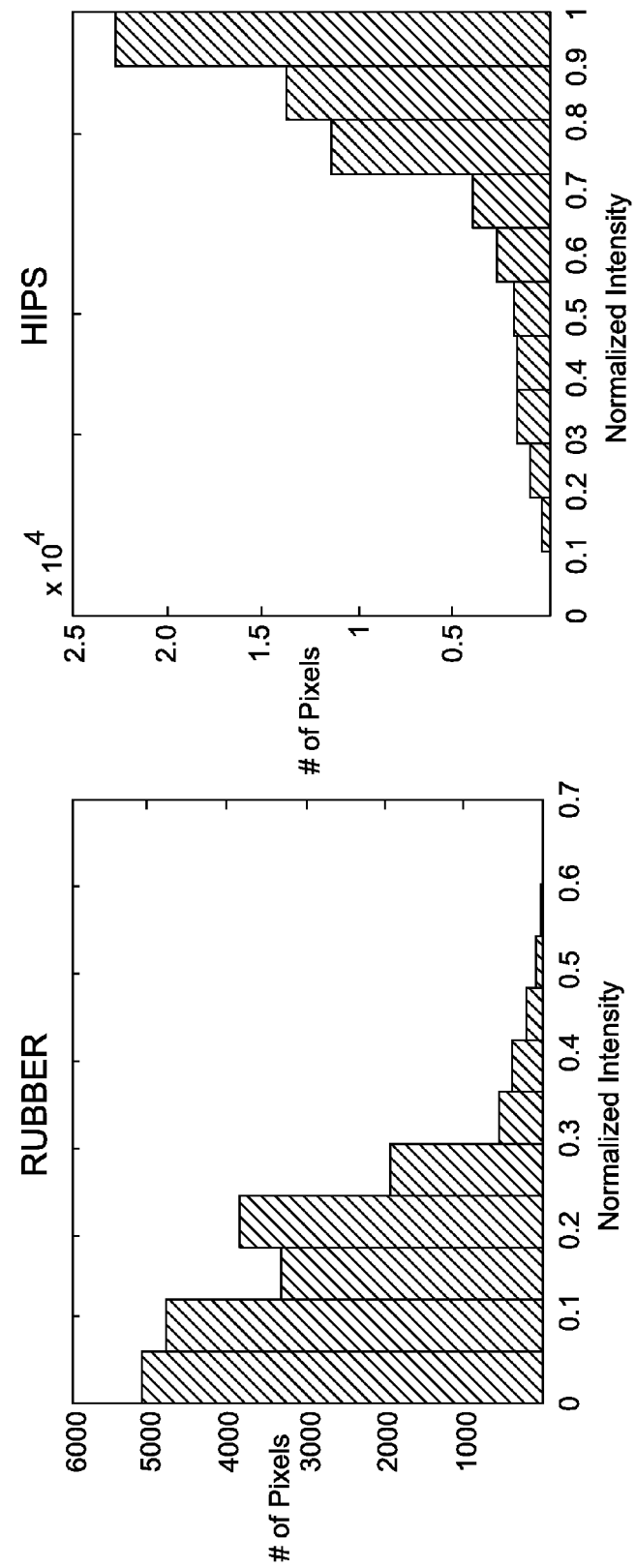
FIG. 6 is an example of histograms of intensity values of imaged pixels, comparing histogram values for black rubber and histogram values for black HIPS plastic.

In particular, FIG. 6 is an example of histograms of intensity values of imaged pixels, comparing histogram values for a black rubber and histogram values for a HIPS plastic. As shown in FIG. 6, the black rubber histogram should be heavily concentrated on the black side due to the lack of specular highlights, while the HIPS histogram should be relatively bright due to its glossiness. In such an example, therefore, the classification can be based on whether the number of high intensity specular reflections is large or the number of high intensity specular reflections is small, as described below.

In step S409, a classifier is calculated based on the feature vector, such as the average intensity of the top 10% of the histogram mass. In particular, material classification can be performed by several methods, using the shape of the histogram for each object. For example, statistical metrics such as kurtosis and skewness are possible candidates for differentiation. As mentioned in step 409, taking the average intensity of the top 10% of the pixel values can also produce robust contrast between the two materials. The percentage value can be adjusted for optimal performance.

Thus, in this example, the classification includes generating a histogram of intensity values of the specular reflections, and differentiating the object from another object by comparing a value of a statistical metric of the object against a value of the statistical metric of another object.

In step S410, the feature vectors are compared using the classifier, by comparing to a threshold to determine the material type of each object. For purposes of conciseness, the following description refers to the statistical metric as an average intensity of a percentage of pixel values of the histogram, as described above with respect to step 409. As mentioned above, a black rubber histogram should be heavily concentrated on the black side due to the lack of specular highlights, while the HIPS histogram should be relatively bright due to its glossiness. A learning process or separate input can be used to determine an appropriate threshold. For example, an average intensity of the top 10% of the pixel values of different objects can be determined by a learning process, and a threshold to differentiate between the two can be obtained therefrom to be applied to histograms of objects to be sorted. Of course, this is simply an example, and the value and type of threshold will depend on the statistical measure being used.

In step S411, if the average intensity of the top 10% of the histogram mass is below the threshold, the object is classified as a matte material such as black rubber. Meanwhile, in step S412, if the average intensity of the top 10% of the histogram mass is above the threshold, the object is classified as a glossy material such as HIPS plastic.

Figure 7:
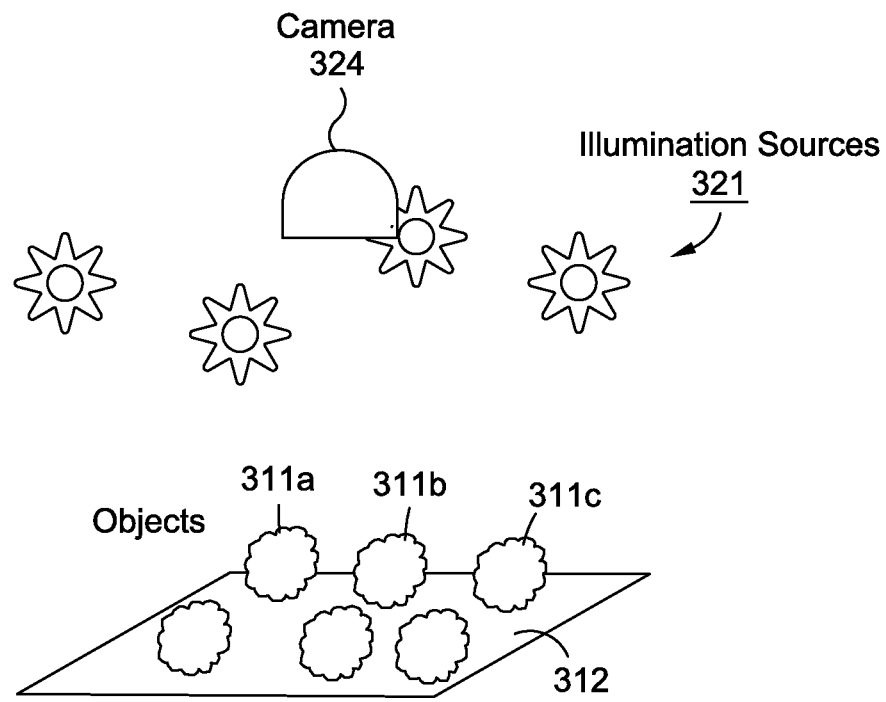
FIG. 7 is an example of another embodiment in which multiple objects are classified simultaneously by simultaneous illumination at a classification station.

FIG. 7 is an example of another embodiment in which multiple objects are classified simultaneously by simultaneous illumination at a classification station.

In particular, as shown in FIG. 7, an imaging surface 312 includes multiple objects placed thereon, such as objects 311a, 311b and 311c. Camera 324 captures an image of the set of objects, which are simultaneously illuminated from multiple angles by illumination sources 321.

<Other Embodiments>

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method of material classification of an object fabricated from an unknown material, said method comprising:
    illuminating the object with an area light source such that the object is illuminated from multiple angles;
    obtaining an image of the illuminated object;
    measuring specular reflections from the object by analyzing the image; and
    classifying the object based on the measured specular reflections,
    wherein classifying the object comprises generating a histogram of intensity values of the specular reflections, and differentiating the object from another object by comparing a value of a statistical metric of the object against a value of the statistical metric of another object, and
    wherein the statistical metric comprises kurtosis or skewness.

2. The method according to claim 1, wherein the classification is based on whether a number of high-intensity specular reflections is large or the number of high-intensity specular reflections is small.

3. The method according to claim 1, wherein the statistical metric also includes an average intensity of a percentage of pixel values of the histogram.

4. The method according to claim 1, wherein the image is processed to increase contrast prior to generating the histogram.

5. The method according to claim 1, wherein the area light source comprises an array of multiple light sources.

6. The method according to claim 1, which differentiates between objects fabricated from materials which have similar spectral signatures but different gloss properties.

7. The method according to claim 6, which differentiates between black-colored objects.

8. The method according to claim 1, wherein an earlier stage of a multi-stage classification process performs material classification based on spectral signatures, and wherein indeterminate objects are delivered for classification according to claim 1.

9. The method according to claim 1, wherein multiple objects are simultaneously classified.

10. An apparatus for material classification of an object fabricated from an unknown material, comprising:
    a computer-readable memory constructed to store computer-executable process steps;
    a processor constructed to execute the computer-executable process steps stored in the memory; and
    wherein the process steps stored in the memory cause the processor to:
    illuminate the object with an area light source such that the object is illuminated from multiple angles;
    obtain an image of the illuminated object;
    measure specular reflections from the object by analyzing the image; and
    classify the object based on the measured specular reflections,
    wherein the process steps which cause the processor to classify the object comprise process steps which cause the processor to generate a histogram of intensity values of the specular reflections, and to differentiate the object from another object by comparing a value of a statistical metric of the object against a value of the statistical metric of another object, and
    wherein the statistical metric comprises kurtosis or skewness.

11. The apparatus according to claim 10, wherein the classification is based on whether a number of high-intensity specular reflections is large or the number of high-intensity specular reflections is small.

12. The apparatus according to claim 10, wherein the statistical metric also includes an average intensity of a percentage of pixel values of the histogram.

13. The apparatus according to claim 10, wherein the image is processed to increase contrast prior to generating the histogram.

14. The apparatus according to claim 10, wherein the area light source comprises an array of multiple light sources.

15. The apparatus according to claim 10, which differentiates between objects fabricated from materials which have similar spectral signatures but different gloss properties.

16. The apparatus according to claim 15, which differentiates between black-colored objects.

17. The apparatus according to claim 10, wherein an earlier stage of a multi-stage classification process performs material classification based on spectral signatures, and wherein indeterminate objects are delivered for classification according to claim 10.

18. The apparatus according to claim 10, wherein multiple objects are simultaneously classified.

19. A non-transitory computer-readable memory medium on which is stored computer-executable process steps for causing a computer to perform material classification of an object fabricated from an unknown material, said process steps comprising:

illuminating the object with an area light source such that the object is illuminated from multiple angles;

obtaining an image of the illuminated object;

measuring specular reflections from the object by analyzing the image; and classifying the object based on the measured specular reflections, wherein classifying the object comprises generating a histogram of intensity values of the specular reflections, and differentiating the object from another object by comparing a value of a statistical metric of the object against a value of the statistical metric of another object, and wherein the statistical metric comprises kurtosis or skewness.

* * * * *